United States Patent [19]

Schwartz

[11] Patent Number: 4,810,651
[45] Date of Patent: Mar. 7, 1989

[54] BLOOD CULTURE ASSEMBLY WITH AN EXTERNALLY ACTUATED VALVE

[75] Inventor: Alan A. Schwartz, Baltimore, Md.

[73] Assignee: Becton, Dickinson and Company, Franklin Lakes, N.J.

[21] Appl. No.: 159,630

[22] Filed: Feb. 23, 1988

[51] Int. Cl.$^4$ .......................... C12N 1/24; F16K 1/16
[52] U.S. Cl. .................................. 435/296; 435/286; 435/299; 220/20.5; 251/228; 251/298
[58] Field of Search ............... 435/284, 285, 286, 296, 435/299; 220/20.5; 215/DIG. 8; 206/221; 251/228, 298, 236, 349, 354

[56] References Cited

U.S. PATENT DOCUMENTS

| | | | |
|---|---|---|---|
| 2,793,776 | 5/1957 | Lipari | 206/221 |
| 2,813,649 | 11/1957 | Lipari | 220/20.5 |
| 2,992,974 | 7/1961 | Belcove et al. | 435/296 |
| 3,416,770 | 12/1968 | Green | 251/354 |
| 3,589,983 | 6/1971 | Holderith et al. | 435/296 |
| 4,171,074 | 10/1979 | Diamond | 251/349 |
| 4,308,347 | 12/1981 | Forrer et al. | 435/299 |
| 4,678,753 | 7/1987 | Hempel et al. | 435/296 |

FOREIGN PATENT DOCUMENTS 19589 of 1892 United Kingdom ............... 251/228

*Primary Examiner*—Samuel Scott
*Assistant Examiner*—Noah Kamen
*Attorney, Agent, or Firm*—Mary M. Allen

[57] ABSTRACT

A culture bottle assembly has a container divided into two compartments by a flange. A closure and flexible septum seals the container from the outside environment. A frame inside the container is moveable between two positions. In one position the two compartments are sealed from each other, and in the second position fluid communication exists between the compartments. The frame has an elongated member and a skirt. The skirt engages the flange to form a seal. Downward force in the elongated member causes the skirt to flex. Cooperating means create a gap between the skirt and the flange when the skirt flexes. The flexible septum covers the elongated member thereby allowing force to be applied to the elongated member without opening the container. A solid media holder has trays for holding solid media in the upper compartment.

13 Claims, 2 Drawing Sheets

4,810,651

BLOOD CULTURE ASSEMBLY WITH AN EXTERNALLY ACTUATED VALVE

FIELD OF THE INVENTION

The present invention relates to a culture bottle assembly wherein a liquid nutrient medium is provided in combination with a solid medium so that a fluid sample can be incubated in the liquid nutrient medium and thereafter the precultured liquid medium is used to inoculate the solid medium and to continue the growth of organisms.

BACKGROUND OF THE INVENTION

The detection of microorganisms in body fluids, particularly bacteria in blood, requires that a sample of the fluid be used to inoculate a liquid nutrient medium. Subsequently, the liquid medium is in turn used to inoculate a solid medium to continue the growth of the organisms and to make them visible to the naked eye as colonies.

Normal monophasic systems consist of a liquid medium in a culture bottle or vial which is inoculated with a sample of the fluid and is then incubated for a desired period of time (24-48 hours). After that, a sample is withdrawn from the bottle and is used to inoculate a solid nutrient medium (e.g. agar in a Petri dish). This procedure is laborious, sometimes hazardous and includes the risk of contamination with microorganisms from the environment. Additionally, the atmosphere above the liquid medium and surrounding the solid media is contaminated with ambient air when the solid media is inoculated. This is undesirable when the microorganism requires an anaerobic environment.

Detection systems have been developed in which liquid and solid culture media are combined in the same container. Such systems avoid the troublesome and sometimes hazardous transfer of the liquid culture to the solid culture medium. U.S. Pat. No. 2,992,974 to Belcove et al, for example, describes a biological testing device in which a solid medium is restrained in the top portion of a rectangular culture bottle while a liquid nutrient medium is provided in the lower most portion of the bottle. U.S. Pat. No. 3,589,983 to Holderith et al describes a culture bottle which is designed to hold a solid agar nutrient material at a location along the axial centerline of a bottle. The bottle also houses a liquid nutrient broth which may be separated from the solid agar by positioning the bottle on its side.

The above described devices which combine a liquid nutrient medium in a single container with a solid medium have a major disadvantage in that the culture assembly must be positioned in a certain manner prior to contacting the solid medium with the precultured liquid medium. The above described devices for separating solid and liquid culture media are complicated and facilitate separation of the liquid media and the solid media only during incubation, but not during transport. These constructions are not suitable for assembly at the point of manufacture because contact between the liquid and solid media during shipping and storage prior to use causes constituents in the solid medium to elute into the liquid medium.

U.S. Pat. No. 4,308,347 to Forrer et al. describes a device for detection of microorganisms in a fluid sample which includes a first container holding a liquid nutrient medium and a second container containing one or more solid nutrient medium. The containers are detachably connected so that the media can be brought into contact when desired. The device described in the Forrer et al. patent is complicated and requires several manipulative steps to bring the precultured liquid media into contact with the solid medium.

A culture bottle assembly for the detection of microorganisms in body fluids is described in U.S. Ser. No. 056,518, filed June 1, 1987 by Hammann. The Hammann culture bottle assembly comprises a single container divided into a first lower compartment and a second upper compartment by a flange on the interior of the container. A frame is provided for insertion into the second upper compartment. The frame has a lower peripheral edge which can be lowered into mating relationship with the flange. A resilient material is disposed on the lower peripheral edge. Closure means are provided which cause the frame to move downwardly and compress the resilient material against the flange to close the container and to seal the two compartments from each other. The first lower compartment contains a liquid nutrient medium and the second upper compartment contains one or more solid media. A fluid conduit is provided through the frame whereby a specimen can be inserted through an aperture in the closure means into the fluid medium in the lower compartment. After a sample is incubated in the liquid medium for a desired period of time the closure means are moved to a second position which provides an open space above the internal flange through which the precultured liquid medium can be transferred into contact with the solid media when the container is turned over. The culture bottle assembly described by Hammann is a vast improvement over earlier devices, but the possibility exists that a person loosening the closure to axially move the frame could turn the closure too far allowing fluid to leak out of the container when the assembly is inverted.

SUMMARY OF THE INVENTION

The present invention is a new valve assembly for use in a culture bottle assembly of the type described in the Hammann application. The valve assembly comprises a valve seat which may be flange, a frame, and cooperating means. The frame has an elongated member having upper and lower ends and a passageway through it. The skirt depends from the lower end of the elongated member. It has a peripheral edge which engages the valve seat to form a seal. The skirt is flexible in response to downward force on the elongated member. The cooperating means creates a gap between the skirt and the valve seat when the skirt flexes in response to downward force on the elongated member. The gap thus created is a fluid passageway.

The cooperating means may conveniently be one or more protuberances depending from the lower surface of the skirt which engage the valve seat when the skirt flexes in response to downward force on the elongated member. Alternatively, the cooperating means may be one or more protuberances extending from the valve seat to engage a lower surface of the skirt when the skirt flexes in response to downward force on the elongated member.

The elongated member and the skirt may be integrally formed or they can be formed separately and joined together at the lower end of the elongated member. When they are integrally formed, the skirt preferably has a flexing section having a cross section thinner than the cross section of the remainder of the skirt.

The culture bottle assembly of the present invention has a container which has a lower compartment and an upper compartment. The two compartments are separated by a valve seat on the interior of the container. A frame in the container has an elongated member with upper and lower ends and a passageway through it. The frame also has a skirt depending from the elongated member. The skirt has a peripheral edge for engaging the valve seat to form a seal. The skirt is flexible in response to downward force on the elongated member. The assembly further includes cooperating means to create a gap between the skirt and the valve seat upon flexing of the skirt. The gap thus created is a fluid passageway. A closure is provided to seal the container from an ambient environment. Means for transmitting force applied externally of the container downward on the elongated member allow a user to inoculate a solid medium in the upper compartment with fluid contained in the lower compartment without opening the container.

In a particularly preferred construction the means for transmitting downward force is a flexible, pierceable septum positioned over the passageway through the elongated member. In this construction a liquid medium in the lower compartment can be inoculated with a sample by injecting the sample through the septum. Thus the culture bottle assembly can be provided with a liquid medium in the lower compartment and one or more solid media in the upper compartment. The atmosphere surrounding the media can be customized to promote growth in the media provided.

In the most preferred construction a holder supports one or more trays which contain solid media. The holder with its trays, the flexible pierceable septum, and the closure are interconnected to form a subassembly. With this construction the solid media can be removed from the culture bottle assembly by loosening the closure and removing the subassembly. This preferred construction containing the culture media can be shipped and stored with the liquid and solid media sealed from each other. The entire process of culturing a sample in liquid medium followed by inoculation and culturing of the solid media can all be accomplished without opening the container. Then if secondary culturing of colonies growing on the solid media is desired, the solid media can easily be removed from the culture bottle assembly.

DETAILED DESCRIPTION OF THE INVENTION

The culture bottle assembly of the present invention includes a container 111 which is divided into a lower compartment 113 and an upper compartment 115 by a valve seat 117. The valve seat 117 may be integrally formed with the bottle or it can be formed separately from the container. When the valve seat 117 is formed separately, it has an exterior with a shape similar to that of the interior of the container (e.g. cylindrical) and an external dimension (e.g. diameter) slightly larger than the internal dimension of the container. With this construction the valve seat can be compression fit in the container. When the container and valve seat are separately formed, the container is preferably made of glass while the valve seat is preferably made of a moldable material such as polyethylene or polypropylene.

Figure 2:
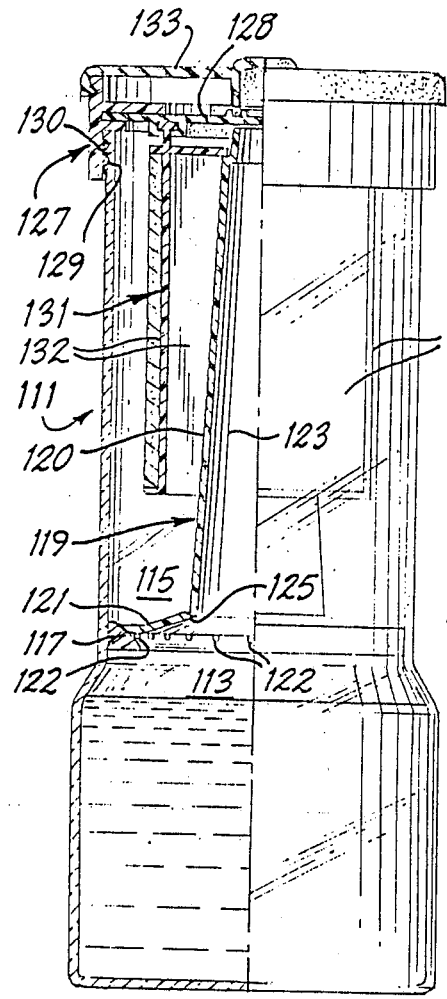
FIG. 2 is a longitudinal partial section of the culture bottle assembly of the present invention with the valve in its sealed position.
Figure 4:
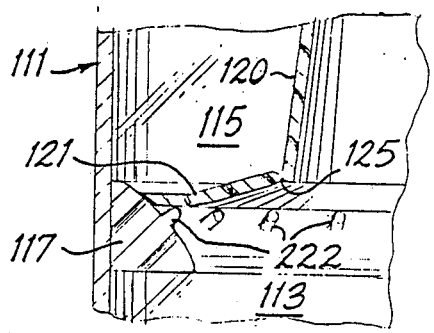
FIG. 4 shows an alternative construction of the valve assembly with the valve in its closed position.

The preferred valve assembly is comprised of a valve seat 117 and a frame 119. The frame 119 is preferably made of a moldable plastic such as polyethylene and has an elongated member 120 and a skirt 121 depending from the elongated member 120. As shown in FIGS. 2 and 4 the skirt 121 engages the valve seat 117 to form a fluid tight seal. The skirt 121 is constructed to be flexible in response to downward pressure on the elongated member 120. Preferably the elongated member 120 and the skirt 121 are integrally formed and the skirt has a flexing section 123 having a cross section thinner than the remainder of the skirt 121.

Figure 1:
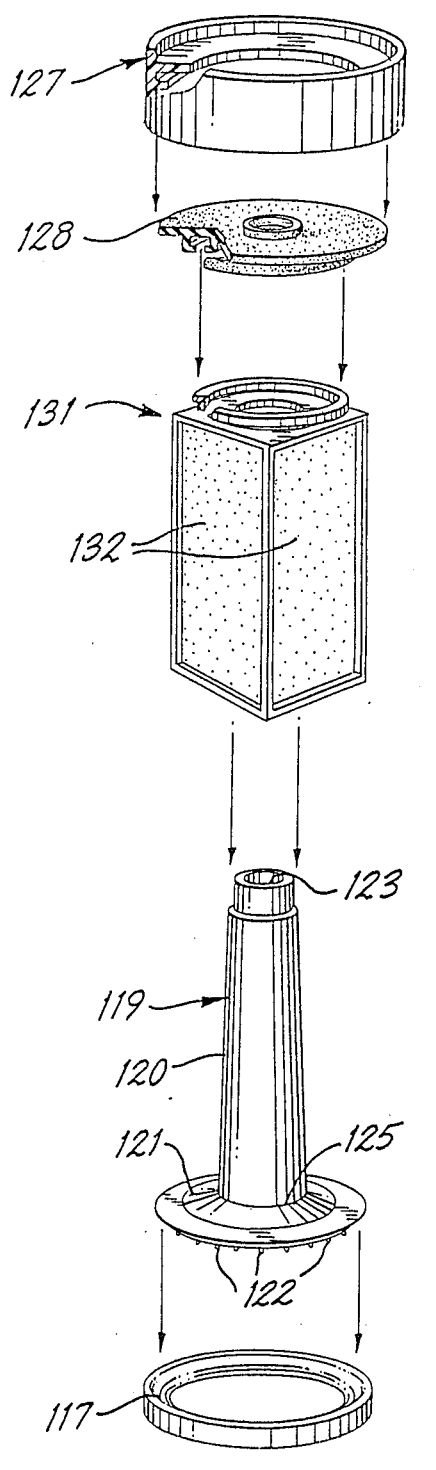
FIG. 1 is an exploded perspective view of the valve of the present invention and a solid media holder.
Figure 3:
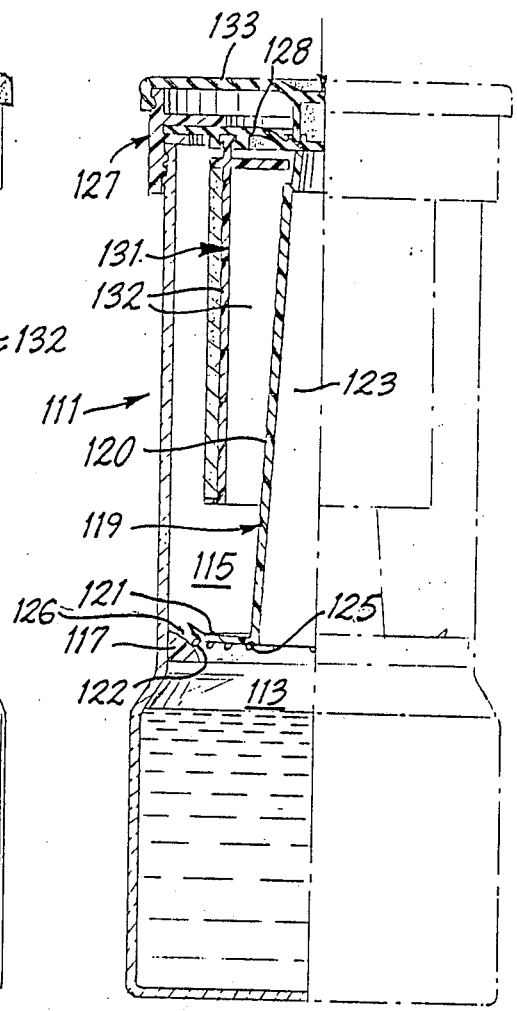
FIG. 3 is a longitudinal partial cross section view of the culture bottle assembly with the valve in its open position.

As shown in FIGS. 1-3, depending from the skirt 121 are a plurality of protuberances 122. These protuberances 122 are cooperating fulcrum means to create a gap 126 between the skirt 121 and the valve seat 117 when the skirt 121 flexes in response to downward force on the elongated member 120. In the preferred construction, sufficient downward force on the elongated member 120 countered by an upward resisting force where the skirt 121 engages the valve seat 117 causes the skirt 121 to rotate about the flexing section 123 and invert to the position shown in FIGS. 3 and 5. As the skirt 121 flexes in response to the downward force on the elongated member 120, the protuberances 122 engage the valve seat 117 to create a gap 126 between the skirt 121 and the valve seat 117. Upon inversion of the culture bottle assembly, fluid in the lower compartment flows into the upper compartment and inoculates solid media contained in that compartment.

Figure 5:
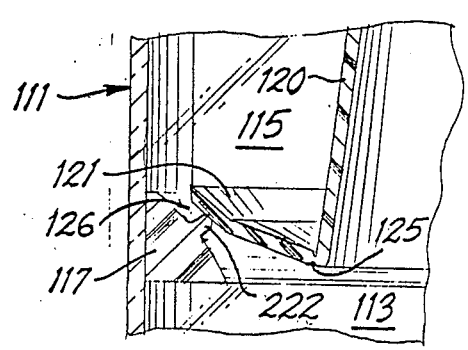
FIG. 5 is the construction of FIG. 4 with the valve in its open position.

An alternative construction of the valve assembly is shown in FIG. 4-5. In this construction, the valve seat 117 includes protuberances 222 which serve as cooperating fulcrum means to create a gap 126 between the skirt 121 and the valve seat 117 upon flexing of the flange in response to downward force on the elongated member 120.

The culture bottle assembly further includes a closure 127 and a flexible, pierceable septum 128. The closure 127 is preferably made of a moldable plastic or metal and has threads 129 in its interior surface which mate with threads 130 on the exterior surface of the container 111. The septum 128 is connected to the closure 127. The closure and septum serve to seal the entire container from an outside environment.

The septum covers the upper end of the elongated member. Because the septum is flexible, force applied to the septum is translated to the elongated member so that the valve assembly can be actuated without opening the container.

A solid media holder 131 has one or more trays for holding solid media. The trays may be integrally formed with the holder or provided separately. As shown in FIGS. 1-3, the holder 131 is connected to the septum 128. The holder has a T shaped projection 134 which mates with a groove 135 on the underside of the septum. The three part subassembly comprising the holder, the septum, and the closure can be removed from the culture bottle assembly as a unit. This subassembly provides a convenient and safe way to handle the solid media when secondary culturing of colonies on the solid media is desired.

A passageway 123 extends through the elongated member 120. When the septum covering the upper end of the elongated member is made of a resealable, pierceable material, a fluid sample can be injected into the lower compartment of the container through the septum and the passageway.

The final element of the preferred construction is a dust cover 133 which protects the septum from the environment during shipping and storage. The dust cover 133 can be removed when a sample is injected into the container. The dust cover can be removed or left in place when the valve is actuated.

The culture bottle assembly is suitable for prefilling with liquid and solid media at the time of manufacture. The choice of liquid and solid media can be customized for the intended use. Thus the assembly can be filled with a liquid medium that will support growth of a broad spectrum of microorganisms and the solid media can contain selective agents so that only microorganisms of a single genus or species will grow. Additionally, when the holder 132 has multiple trays 133, multiple solid media can be used.

In accordance with the present invention an extremely simple device is provided for transporting a container prefilled with both liquid and solid media and for culturing a sample in the liquid medium followed by inoculation of the solid medium with the precultured liquid medium. The culture bottle assembly of the present invention permits transportation of the liquid medium and the solid medium in separate sealed compartments and provides easy means for transferring the precultured liquid medium into contact with the solid medium when desired.

What is claimed is:

1. A valve assembly comprising:
   a valve seat; and
   a frame having
      an elongated member with upper and lower ends and a passageway therethrough;
      a skirt pivotably connected to the lower end of the elongated member, the skirt having a peripheral edge for engaging the valve seat to form a seal wherein the elongated member is disposed on an upperside of the skirt and the valve seat is located on a lower side of the skirt and the peripheral edge of the skirt being pivotable in response to downward force on the elongated member, and cooperating fulcrum means to create a gap between the skirt and the valve seat upon pivoting of the peripheral edge of the skirt to create a fluid passageway.

2. The valve assembly of claim 1 wherein the cooperating means is at least one protuberance depending from a lower surface of the skirt for engaging the valve seat when downward force is exerted on the elongated member.

3. The valve assembly of claim 1 wherein the cooperating means is at least one protuberance extending from the valve seat to engage the skirt when downward force is exerted on the elongated member.

4. The valve assembly of claim 1 wherein the cooperating means is a plurality of protuberances depending from a lower surface of the skirt for engaging the valve seat when downward force is exerted on the elongated member.

5. The valve assembly of claim 1 wherein the elongated member and the skirt are integrally formed and the skirt has a flexing section with a thinner cross section than the cross section of the remainder of the skirt.

6. A culture bottle assembly comprising:
   a container having a lower compartment and an upper compartment;
   a valve seat on the interior of the container between the lower compartment and the upper compartment;
   a frame having
      an elongated member with upper and lower ends and a passageway therethough, and
      a skirt depending from the lower end of the elongated member, the skirt having a peripheral edge for engaging the valve seat to form a seal and the peripheral edge of the skirt being pivotable in response to downward force on the elongated member;
   cooperating fulcrum means to create a gap between the skirt and the valve seat upon pivoting of the peripheral edge of the skirt to create a fluid passageway;
   a closure for sealing the container from an ambient environment; and
   the closure including means for transmitting force exerted externally of the container downward on the elongated member and being accessible without opening the container.

7. The culture bottle assembly of claim 6 wherein the cooperating means is at least one protuberance on a lower surface of the skirt for engaging the valve seat when downward force is exerted on the elongated member.

8. The culture bottle assembly of claim 6 wherein the cooperating means is at least one protuberance on the valve seat for engaging a lower surface of the valve seat when downward force is exerted on the elongated member.

9. The culture bottle assembly of claim 6 wherein the cooperating means is a plurality of protuberances depending from a lower surface of the skirt for engaging the valve seat when downward force is exerted on the elongated member.

10. The culture bottle assembly of claim 6 wherein the means for transmitting downward force is a flexible, pierceable septum positioned over the passageway so that a sample can be inoculated into the lower compartment through the septum and the passageway without opening the container.

11. The culture bottle assembly of claim 6 further comprising a liquid culture media in the lower compartment and a holder having at least one tray containing a solid medium in the upper compartment.

12. The culture bottle assembly of claim 6 further comprising a liquid culture medium in the lower compartment and a holder containing a plurality of trays, each tray holding a solid media in the upper compartment.

13. The culture bottle assembly of claim 12 wherein the holder, the means for transmitting downward pressure and the closure are interconnected so that they can be removed from the assembly as a single unit.

* * * * *